United States Patent
Coyne et al.

(10) Patent No.: US 11,826,266 B2
(45) Date of Patent: Nov. 28, 2023

(54) BONE WEDGE DEVICE AND METHOD

(71) Applicant: NEXTREMITY SOLUTIONS, INC., Warsaw, IN (US)

(72) Inventors: Matthew Coyne, Warsaw, IN (US); Adam Finley, Warsaw, IN (US)

(73) Assignee: MEDARTIS AG, Basel (CH)

( * ) Notice: Subject to any disclaimer, the term of this patent is extended or adjusted under 35 U.S.C. 154(b) by 216 days.

(21) Appl. No.: 17/367,976

(22) Filed: Jul. 6, 2021

(65) Prior Publication Data

US 2022/0008220 A1    Jan. 13, 2022

Related U.S. Application Data

(60) Provisional application No. 63/049,243, filed on Jul. 8, 2020.

(51) Int. Cl.
| | |
|---|---|
| *A61F 2/46* | (2006.01) |
| *A61B 17/80* | (2006.01) |
| *A61F 2/42* | (2006.01) |
| *A61B 17/16* | (2006.01) |
| *A61F 2/30* | (2006.01) |
| *A61B 17/88* | (2006.01) |

(52) U.S. Cl.
CPC ........ *A61F 2/4606* (2013.01); *A61B 17/1682* (2013.01); *A61B 17/8095* (2013.01); *A61B 17/88* (2013.01); *A61F 2/30734* (2013.01); *A61F 2/4225* (2013.01); *A61F 2002/30736* (2013.01); *A61F 2002/4223* (2013.01)

(58) Field of Classification Search
CPC ....... A61B 17/8095; A61B 17/88; A61F 2/42; A61F 2002/4223; A61F 2/4225; A61F 2/44; A61F 2/4425; A61F 2/4455; A61F 2/4606
See application file for complete search history.

(56) References Cited

U.S. PATENT DOCUMENTS

| | | | | |
|---|---|---|---|---|
| 8,100,972 | B1 * | 1/2012 | Bruffey | A61F 2/4465 623/17.11 |
| 8,545,562 | B1 * | 10/2013 | Materna | A61F 2/442 623/17.11 |
| 8,900,310 | B2 * | 12/2014 | Carlson | A61F 2/446 623/17.16 |
| 10,441,433 | B2 * | 10/2019 | Patel | A61F 2/4455 |
| 2017/0181781 | A1 | 6/2017 | Dubois et al. | |

(Continued)

*Primary Examiner* — Larry E Waggle, Jr.
(74) *Attorney, Agent, or Firm* — Heslin Rothenberg Farley & Mesiti P.C.

(57) ABSTRACT

An osteotomy implant device includes a housing defining a cavity and having a central plane extending therethrough. The housing includes a first bone engaging surface and a second bone engaging surface. The second bone engaging surface disposed on an opposing side of the central plane from the first bone engaging surface. The osteotomy implant device also includes a cutting member. The cutting member rotatable coupled to the housing. The cutting member rotatable about an axis between a first position and a second position. The cutting member entirely disposed within the cavity between the first bone engaging surface and the second bone engaging surface in the first position. A portion of the cutting member extends beyond at least the first bone engaging surface or the second bone engaging surface of the housing in the second position.

8 Claims, 14 Drawing Sheets

(56) References Cited

U.S. PATENT DOCUMENTS

2017/0312095 A9   11/2017  Patel et al.
2019/0090922 A1    3/2019  Bluchel
2020/0046513 A1    2/2020  Castro
2020/0179135 A1*   6/2020  Castro .................. A61F 2/4455

\* cited by examiner

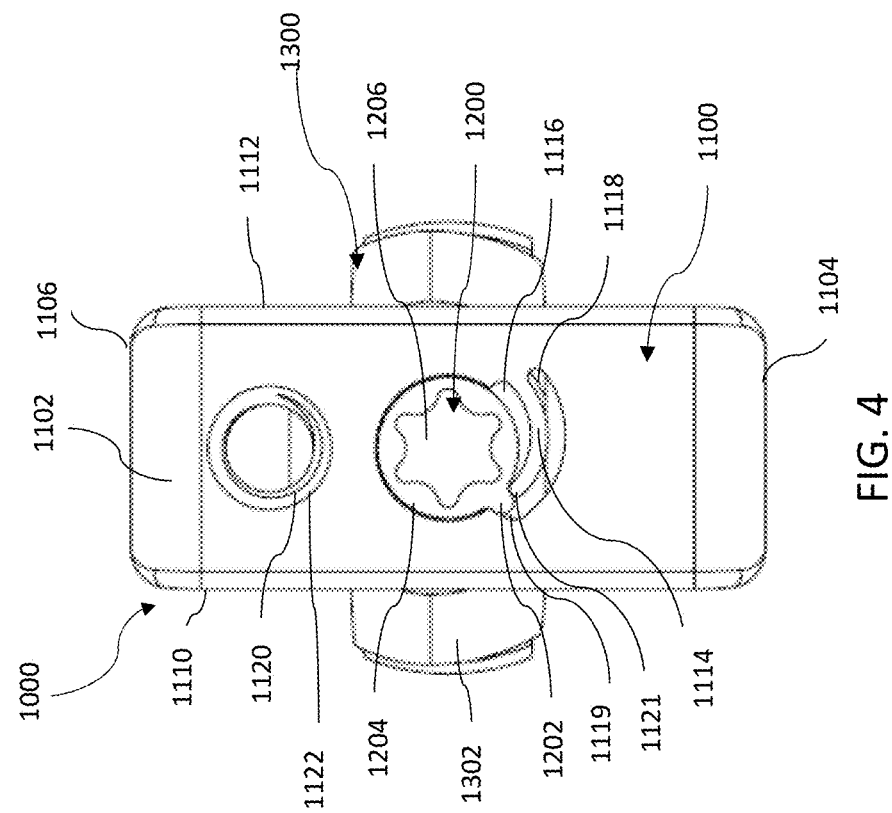
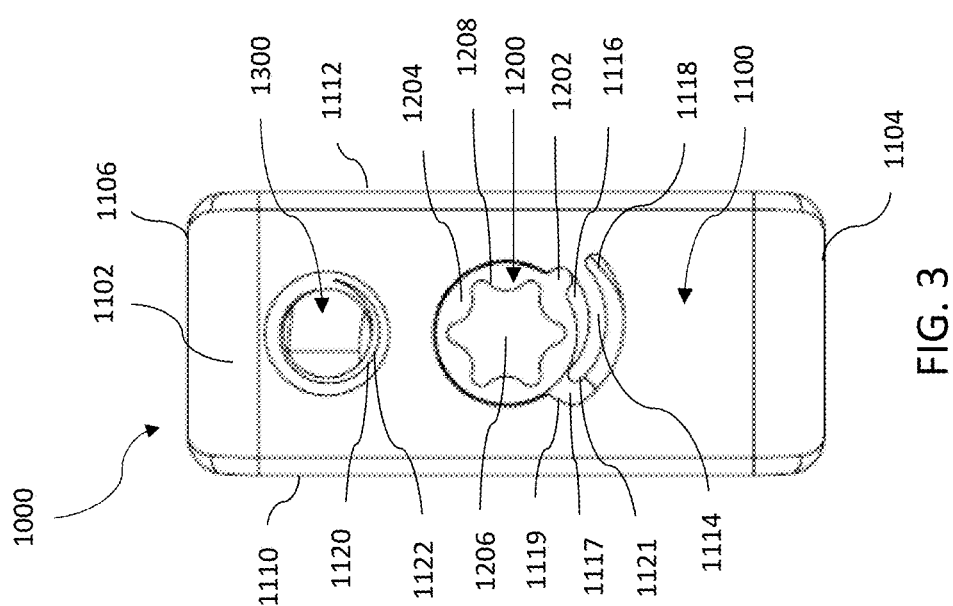

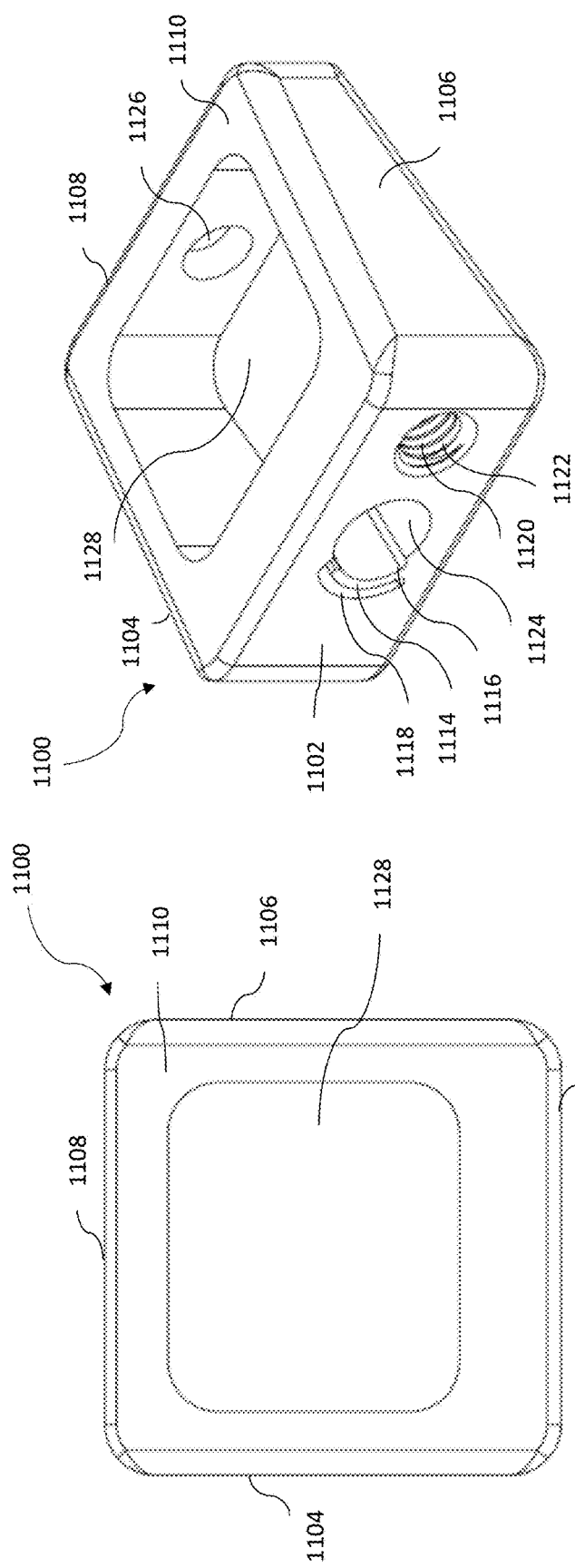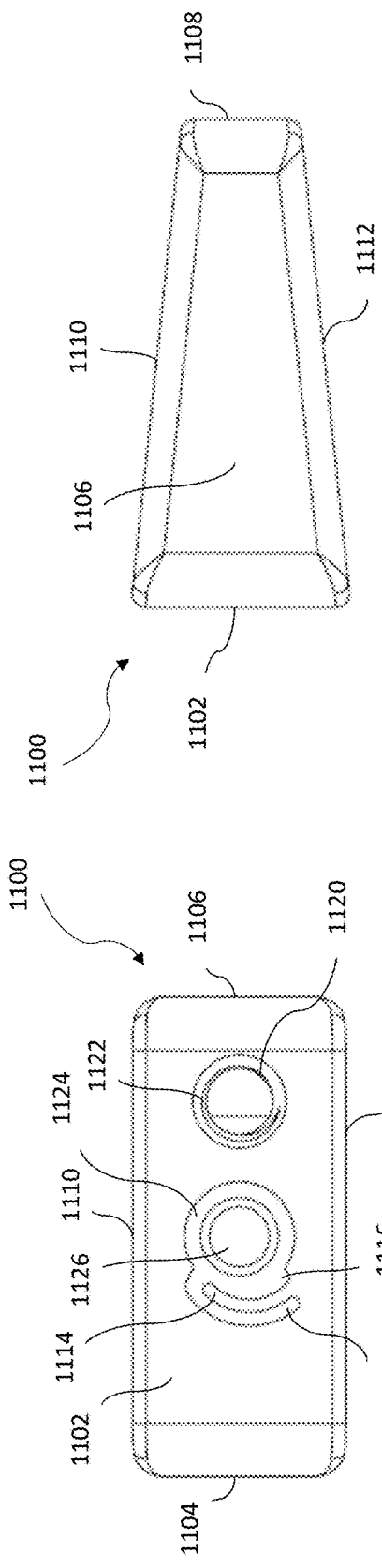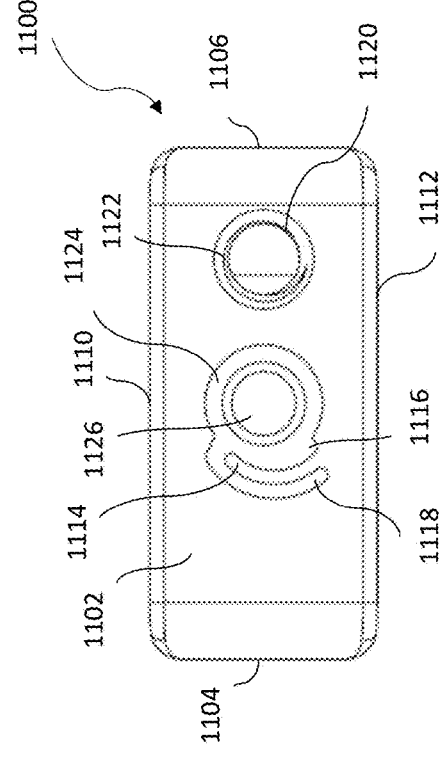

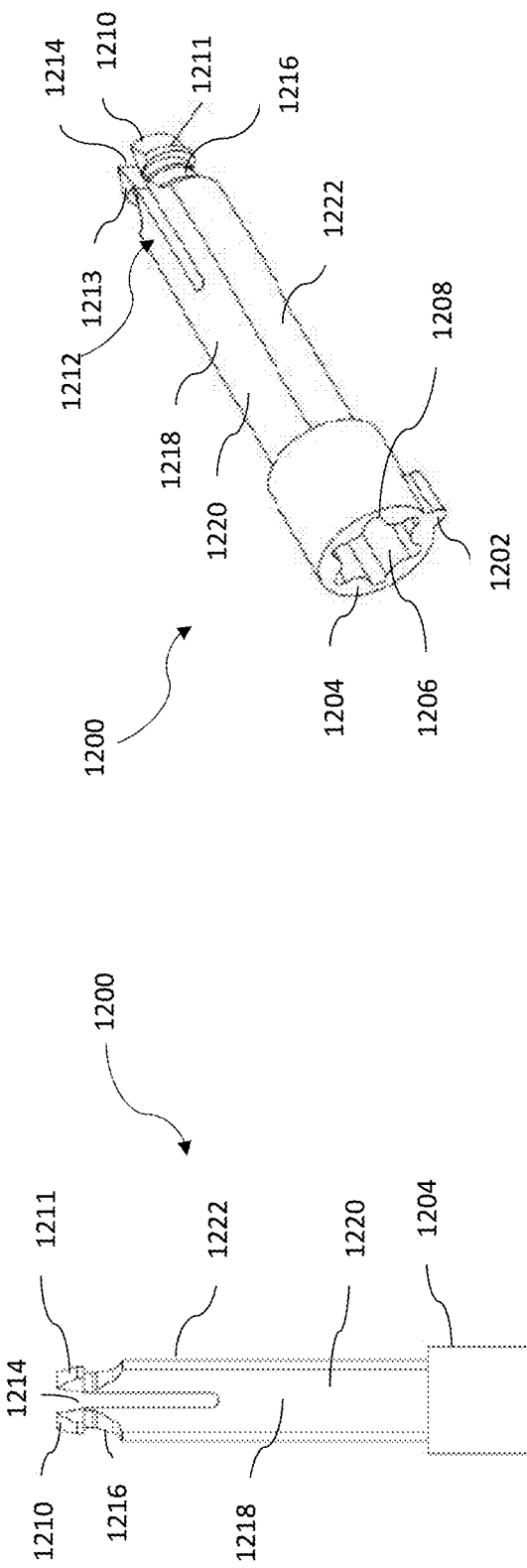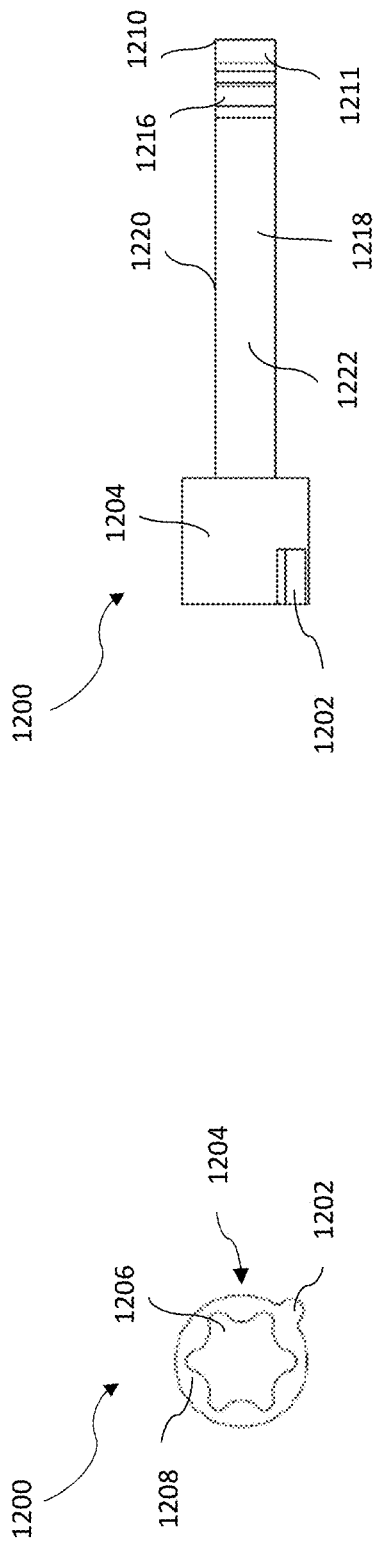

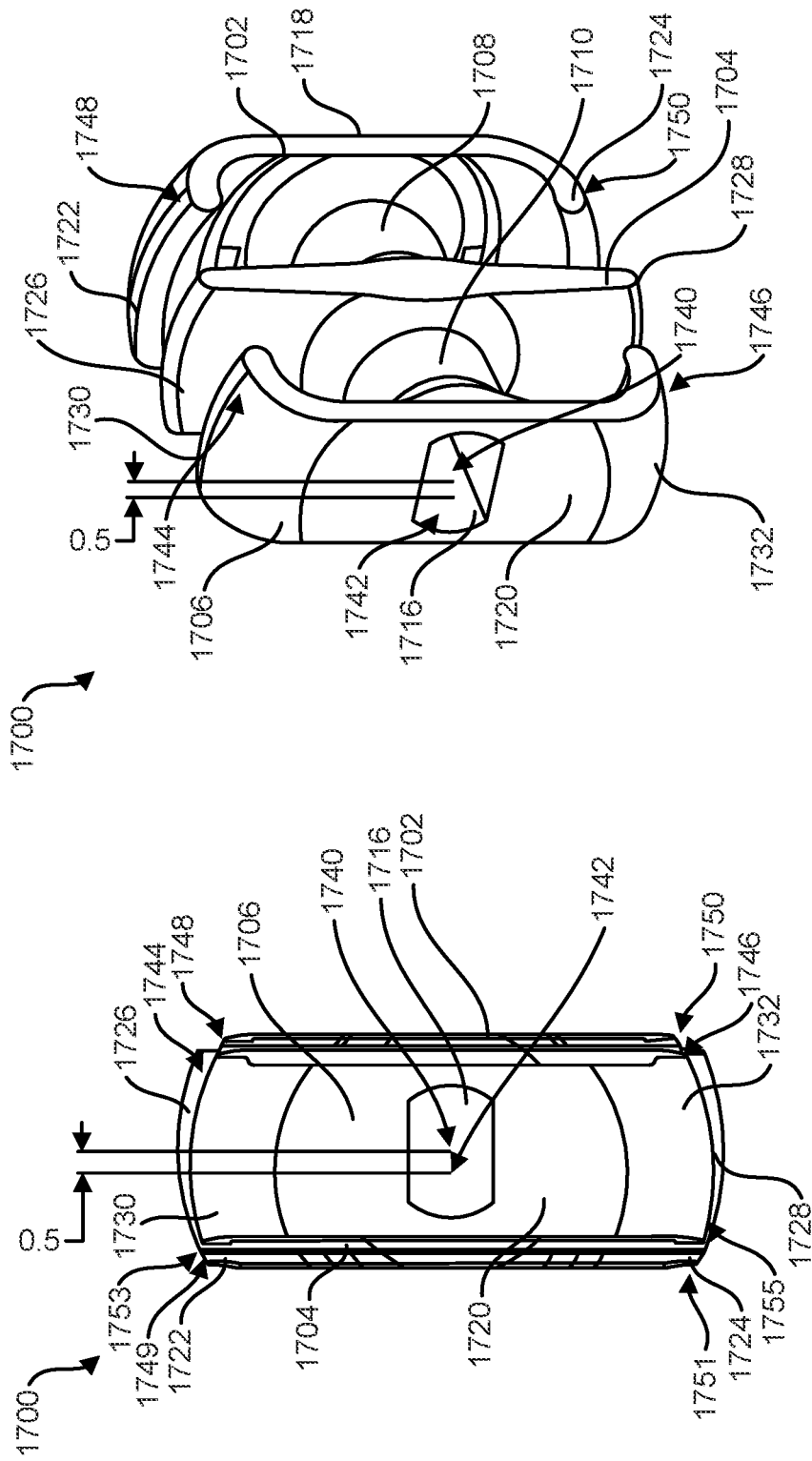

BONE WEDGE DEVICE AND METHOD

CROSS-REFERENCE TO RELATED APPLICATIONS

The present application claims priority to U.S. Provisional Application Ser. No. 63/049,243 filed on Jul. 8, 2020, which is incorporated herein by reference in its entirety.

BACKGROUND

Field of the Invention

This application relates to devices, and methods associated with surgical instruments, and more particularly devices, and methods for bone implants.

Description of the Related Art

Foot anatomy and the proper positioning of bones in the foot are important for providing proper weight bearing, balance, and mobility. Pes planus, commonly known as flatfoot, is a postural deformity that occurs when the arch of the foot is absent while standing and can be painful when performing physical activity such as standing for long periods of time, walking long distances, and/or running. A variety of foot problems, e.g. improper bone development, posterior tibial tendon dysfunction (PTTD), arthritis, injury, or diabetic collapse may cause flatfoot. Often, orthotics, braces, and/or physical therapy are used to treat flatfoot. However, in some cases, additional surgical procedures may be needed to correct anatomical abnormalities associated with flatfoot and provide proper bone positioning to reduce pain and improve mobility.

Osteotomies, surgical procedures in which a bone is cut to shorten, lengthen, or otherwise change bone alignment, are often used to treat flatfoot. Common surgical techniques to treat flatfoot include the Evans calcaneal osteotomy or the Cotton osteotomy, which are osteotomies used to open bones and position autogenous bone (bones harvested from the patient's body), allografts (bones obtained from a bone bank), or synthetic wedges into the bone openings. The Evans calcaneal osteotomy may be used to insert a trapezoidal-shaped implant, i.e. wedge, into the lateral side of the calcaneus, i.e. heel bone, to provide lateral column lengthening. The Cotton osteotomy, which is a medial opening wedge osteotomy, may be used to insert a trapezoidal-shaped implant, i.e. wedge, into the medial cuneiform, which is a bone situated at the medial side of the midfoot, to reduce midfoot abduction.

Often the bones apply high compressive forces to the surgically inserted wedges. In order to maintain a desired wedge position, existing processes use various hardware, such as surgical staples, metal screws and plates, to lock the wedge into place. However, in some patients, the hardware used to maintain the wedge position, such as staples, screws, and plates, may become prominent or irritate nearby tendon or other soft tissue, which may lead to swelling and inflammation.

Thus, a need exists for improved devices, and methods for treating foot deformities such as flatfoot.

SUMMARY OF THE INVENTION

Briefly, an osteotomy implant device constructed in accordance with one or more aspects of the present invention provides, for example, an improved device for treating foot deformities such as, for example, flat foot.

In one embodiment, an osteotomy implant device constructed in accordance with one or more aspects of the present invention includes a wedge shaped housing and a cutting member. The wedge shaped housing defines a cavity and has a central plane extending therethrough. The wedge shaped housing includes a first bone engaging surface and a second bone engaging surface. The first bone engaging surface extends at an acute angle relative to the central plane on a first side of the wedge shaped housing. The second bone engaging surface is disposed on an opposing side of the central plane from the first bone engaging surface on a second side of the wedge shaped housing. The cutting member is rotatable coupled to the wedge shaped housing. The cutting member is rotatable about an axis between a first position and a second position. The cutting member is entirely disposed within the cavity between the first side and the second side in the first position. A portion of the cutting member extends beyond at least the first side or the second side of the wedge shaped housing in the second position.

In one embodiment, at least one of the plurality of fins includes a hook portion.

In another embodiment, a method for wedge osteotomy of a foot is provided. The method includes the stops of exposing a portion of the foot and providing an osteotomy implant device. The osteotomy implant device comprises a housing, a drive shaft and a cutting member. The housing defines a cavity and has a central plane extending therethrough. The housing includes a first side and a second side. The second side is disposed on an opposing side of the central plane from the first side. The drive shaft is rotatably coupled to the housing. The drive shaft includes a head defining a socket. The cutting member is coupled to and rotatable with the drive shaft. The cutting member is rotatable between a first position and a second position. The cutting member includes a plurality of fins extending radially outward. The plurality of fins is entirely disposed within the cavity between the first side and the second side in the first position. At least a portion of the plurality of fins extends beyond at least the first side or the second side of the housing in the second position. The method further includes the steps of inserting the osteotomy implant device in the first position into bone in the exposed portion of the foot, inserting a driver into the socket of the head of said drive shaft, and rotating the driver which rotates said drive shaft and cutting member towards the second position so that the plurality of fins engage the bone.

These, and other objects, features and advantages of this invention will become apparent from the following detailed description of the various aspects of the invention taken in conjunction with the accompanying drawings.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings:

FIG. 3 is a first side view of the device of FIG. 1 having the cutting member disengaged, in accordance with an aspect of the present disclosure;

FIG. 4 is a first side view of the device of FIG. 1 having the cutting member in an engaged position, in accordance with an aspect of the present disclosure;

FIG. 11 is a top view of a wedge housing of the device of FIG. 1, in accordance with an aspect of the present disclosure;

FIG. 12 is a first perspective view of the wedge housing of the device of FIG. 1, in accordance with an aspect of the present disclosure;

FIG. 13 is a first side view of the wedge housing of the device of FIG. 1, in accordance with an aspect of the present disclosure;

FIG. 14 is a second side view of the wedge housing of the device of FIG. 1, in accordance with an aspect of the present disclosure;

FIG. 15 is a top view of a drive shaft of the device of FIG. 1, in accordance with an aspect of the present disclosure;

FIG. 16 is a first perspective view of the drive shaft of the device of FIG. 1, in accordance with an aspect of the present disclosure;

FIG. 17 is a first side view of the drive shaft of the device of FIG. 1, in accordance with an aspect of the present disclosure;

FIG. 18 is a second side view of the drive shaft of the device of FIG. 1, in accordance with an aspect of the present disclosure;

FIG. 23 is a third side view of an alternate cutting member for the device of FIG. 1, in accordance with an aspect of the present disclosure;

FIG. 24 is a third perspective view of the alternate cutting member for the device of FIG. 1, in accordance with an aspect of the present disclosure;

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Figure 2:
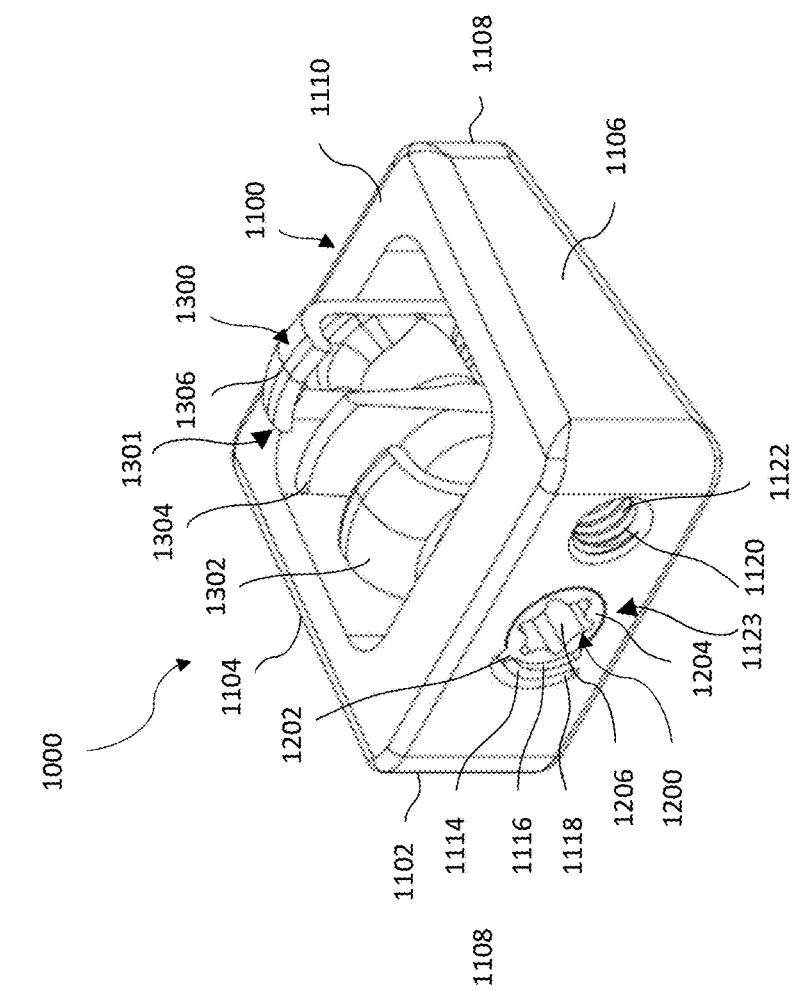
FIG. 2 is a first perspective view of the device of FIG. 1 with the cutting member in an engaged position, in accordance with an aspect of the present disclosure.
Figure 1:
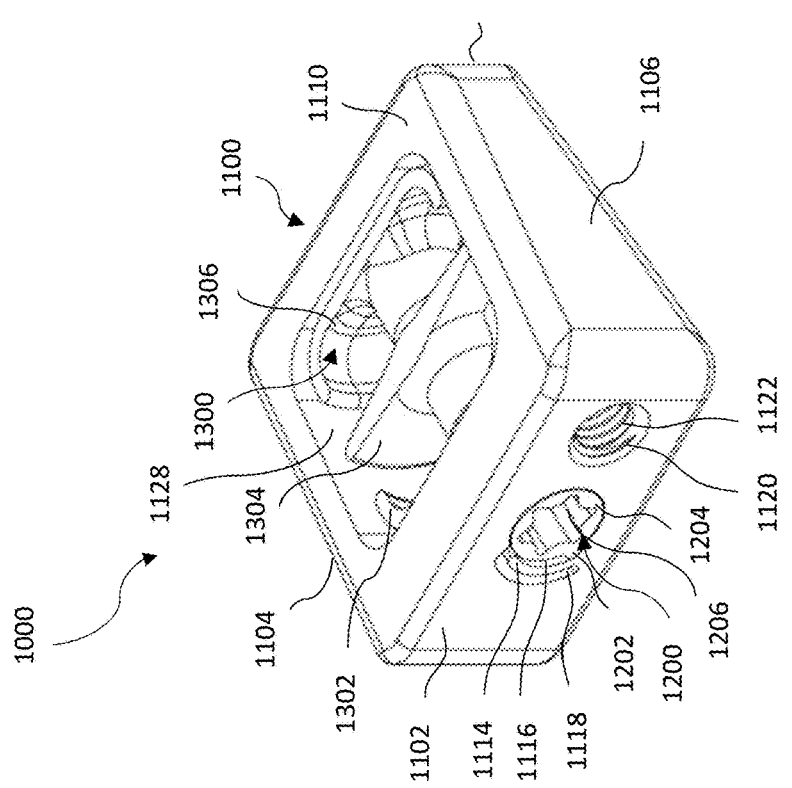
FIG. 1 is a first perspective view of a bone wedge device having a cutting member disengaged, in accordance with an aspect of the present disclosure.
Figure 6:
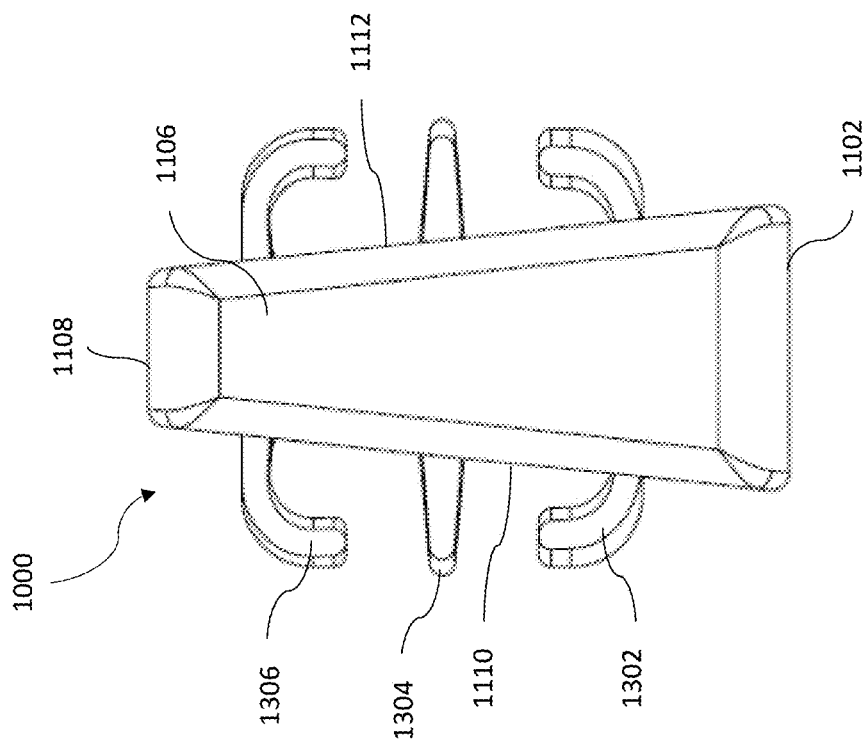
FIG. 6 is a second side view of the device of FIG. 1 having the cutting member in an engaged position, in accordance with an aspect of the present disclosure.
Figure 5:
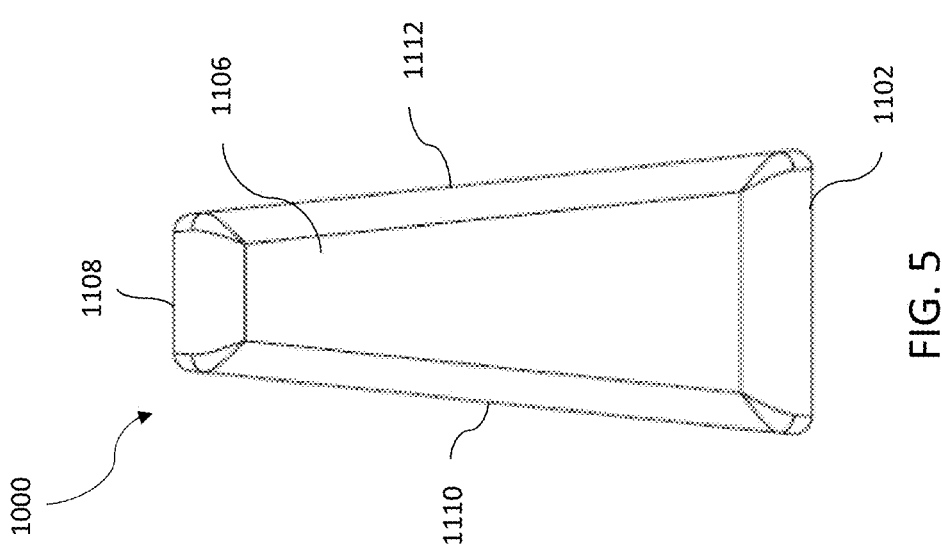
FIG. 5 is a second side view of the device of FIG. 1 having the cutting member in a disengaged position, in accordance with an aspect of the present disclosure.
Figure 8:
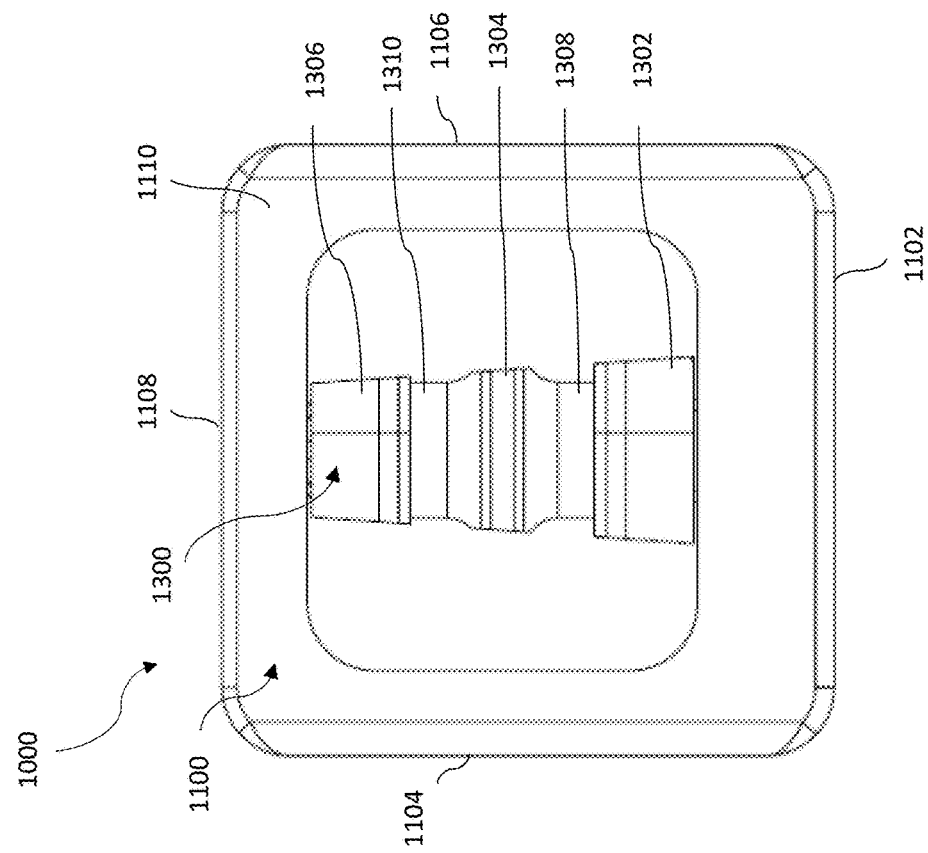
FIG. 8 is a top view of the device of FIG. 1, with the cutting member being in an engaged position, in accordance with an aspect of the present disclosure.
Figure 7:
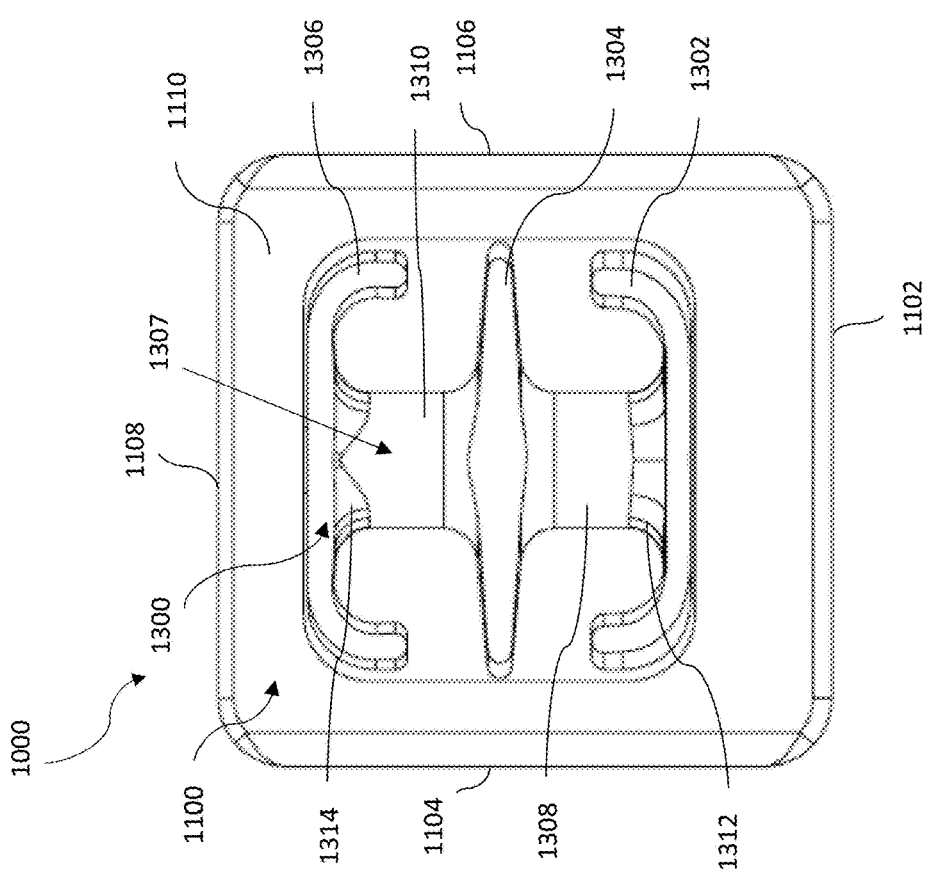
FIG. 7 is a top view of the device of FIG. 1, with the cutting member in a disengaged position, in accordance with an aspect of the present disclosure.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for cutting tools for orthopedic surgery involving a foot or lower extremities. However, those possessing an ordinary level of skill in the relevant art will appreciate that other extremities, joints, and parts of the musculoskeletal system are suitable for use with the foregoing systems, methods and apparatuses. Likewise, the various figures, steps, procedures and workflows are presented only as an example and in no way limit the systems, methods or apparatuses described to performing their respective tasks or outcomes in different timeframes or orders. The teachings of the present invention may be applied to any orthopedic surgery, such as on the hand as well as other upper and lower extremities and may be implemented in other treatments sites that have similar anatomical considerations.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 9:
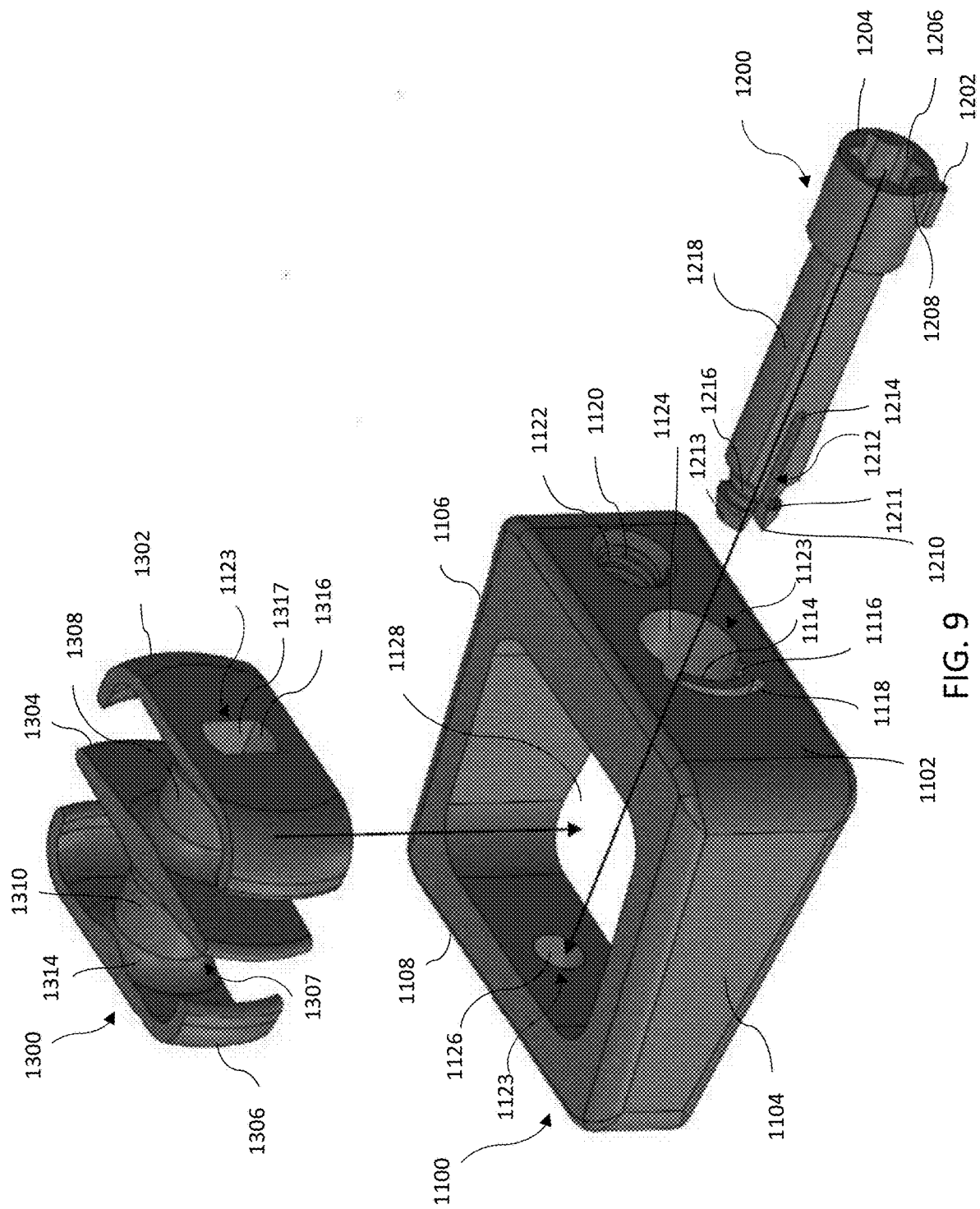
FIG. 9 is an exploded second perspective view of the device of FIG. 1, in accordance with an aspect of the present disclosure.

As will be described below, the present invention includes devices and methods for correcting a deformity of the human foot. As depicted in FIGS. 1-33, a bone wedge device 1000 may include a wedge housing 1100, a drive shaft 1200, and a cutting member 1300. Wedge housing 1100 may include, for example, a central cavity 1128 for housing cutting member 1300 and a plurality of apertures 1123 (FIG. 9). Apertures 1123 may be, for example, sized and shaped or configured to receive drive shaft 1200 such that drive shaft 1200 may be inserted through apertures 1123. Additionally, cutting member 1300 may include a hollow channel 1316 (FIG. 9) that may be, for example, sized and shaped or configured to receive drive shaft 1200 such that drive shaft 1200 may be inserted through hollow channel 1316 in addition to apertures 1123, thereby attaching cutting member 1300 to wedge housing 1100.

Drive shaft 1200 may be rotatable within a first circular aperture 1124 and a second circular aperture 1126 (FIGS. 1-8) of apertures 1123 of wedge housing 1100. In particular, drive shaft 1200 may rotate cutting member 1300 about a central axis of wedge housing 1000 such that cutting member 1300 becomes engaged with a bone 901 such as, e.g., a medial cuneiform 902 (FIGS. 29-33) of a foot 900 (FIGS. 29-33) of the patient and/or a calcaneus 904 (FIGS. 29-33) of foot 900 of the patient. Cutting member 1300 (FIGS. 1-8) may be capable of and configured (e.g., shaped and dimensioned) to cut into bone 901 (FIGS. 29-33) of foot 900 (FIGS. 29-33) to retain positioning of bone wedge device 1000 relative to bone 901 (FIGS. 29-33) of foot 900 (FIGS. 29-33). In particular, cutting member 1300 (FIGS. 1-8) may inhibit migration of bone wedge device 1000 and prevent displacement of bone wedge device 1000 due to decompression of bone 901 (FIGS. 29-33) once an osteotomy procedure is performed. The osteotomy procedures performed may include the Evans calcaneal osteotomy and/or the Cotton osteotomy.

As depicted in FIGS. 1-8, wedge housing 1100 of bone wedge device 1000 may include a first side 1102, a second side 1106, a third side 1108, a fourth side 1104, a top side 1110, and a bottom side 1112. First side 1102 may include a flexible appendage 1114 that is, for example, sized and shaped or configured to flexibly move within a first channel 1116 and a second channel 1118 as depicted in FIGS. 3-4, for example. For instance, flexible appendage 1114 may be displaced into second channel 1118 by a protrusion 1202 on a head 1204 of drive shaft 1200 due to rotation of drive shaft 1200. In particular, when drive shaft 1200 is turned in, for example, a clockwise direction to engage cutting member 1300, protrusion 1202 may gradually apply pressure to flexible appendage 1114 as drive shaft 1200 is turned such that flexible appendage 1114 is gradually displaced into second channel 1118. Head 1204 of drive shaft 1200 may include a socket or hollow 1206 that is, for example, sized and shaped or configured for receiving a driver (not shown) or other tool used to turn drive shaft 1200. For example, hollow 1206 of drive shaft 1200 may include a tongue and groove shape or another interlocking pattern, such as, e.g., a pattern 1208, to engage the driver (not shown) such that drive shaft 1200 may be rotated. In particular, drive shaft 1200 may be rotated to position cutting member 1300 in an engaged position with, for example, bone 901 (FIGS. 29-33).

Rotation of drive shaft 1200 may be stopped by a channel wall 1119 of wedge housing 1100. Channel wall 1119 may located at an end of first channel 1116 and second channel 1118 at a distance from a tip end 1121 of flexible appendage 1114 forming a pocket 1117 that is, for example, sized and shaped or configured to receive protrusion 1202 on head 1204 of drive shaft 1200. Once rotation of drive shaft 1200 is stopped, e.g. when protrusion 1202 hits channel wall 1119 and rests in pocket 1117, flexible appendage 1114 may snap back towards channel 1116 and return to an initial resting position. In particular, the initial resting position may be where flexible appendage 1114 was initially located prior to being displaced by protrusion 1202 during rotation of drive shaft 1200. Once protrusion 1202 is positioned in pocket 1117 and flexible appendage 1114 snaps back to its initial position, the repositioning of flexible appendage 1114 may lock drive shaft 1200 in place so that cutting member 1300 remains in an engaged position with, for example, bone 901 (FIGS. 29-33).

Wedge housing 1100 may also include an installation aperture 1120 that is sized and shaped or configured for receiving an installer or other instrument (not shown). For instance, installation aperture 1120 may include a threaded surface 1122 with which the installer may engage during surgical insertion of bone wedge device 1000.

Further, as shown in FIGS. 1-8, rotation of drive shaft 1200 causes cutting member 1300 to rotate about a central axis of wedge housing 1100. For instance, rotating cutting member 1300 about the central axis when bone wedge device 1000 is being implanted may facilitate fixating bone wedge device 1000 in place so that a position of bone wedge device 1000 may be maintained to avoid expulsion of bone wedge device 1000 from the osteotomy. For example, cutting member 1300 may be rotated 90° about the central axis of wedge housing 1100 to fully engage the bone and reduce movement of bone wedge device 1000 relative to the bone. Cutting member 1300 may include a plurality of fins or arms 1301 (FIG. 2) extending from a central cylinder 1307 (FIG. 7), with central cylinder 1307 extending from a first arm 1302 of arms 1301 of cutting member 1300, through a centralized second arm 1304 of arms 1301 of cutting member 1300, to a third arm 1306 of arms 1301 of cutting member 1300 as depicted, for example, in FIGS. 7-8. First arm 1302 may be separated from second arm 1304 by a first segment 1308 of central cylinder 1307, and second arm 1304 may be separated from third arm 1306 by a second segment 1310 of central cylinder 1307. Additionally, a first sloping portion 1312, or a portion of first sloping portion 1312, may connect first arm 1302 to first segment 1308 and a second sloping portion 1314, or a portion of second sloping portion

1314, may connect third arm 1306 to second segment 1310. Cutting member 1300 may, for example, rotate clockwise based on drive shaft 1200 being rotated in a clockwise direction. According to one embodiment, first arm 1302 and third arm 1306 may be curved or hooked inward toward second arm 1304. The hook configuration of first arm 1302 and third arm 1306 may facilitate holding bone wedge device 1000 close to the bone to impede separation from the bone or inhibit migration to inhibit expulsion of bone wedge device 1000 once implanted and to avoid decompression of the osteotomy.

Figure 10:
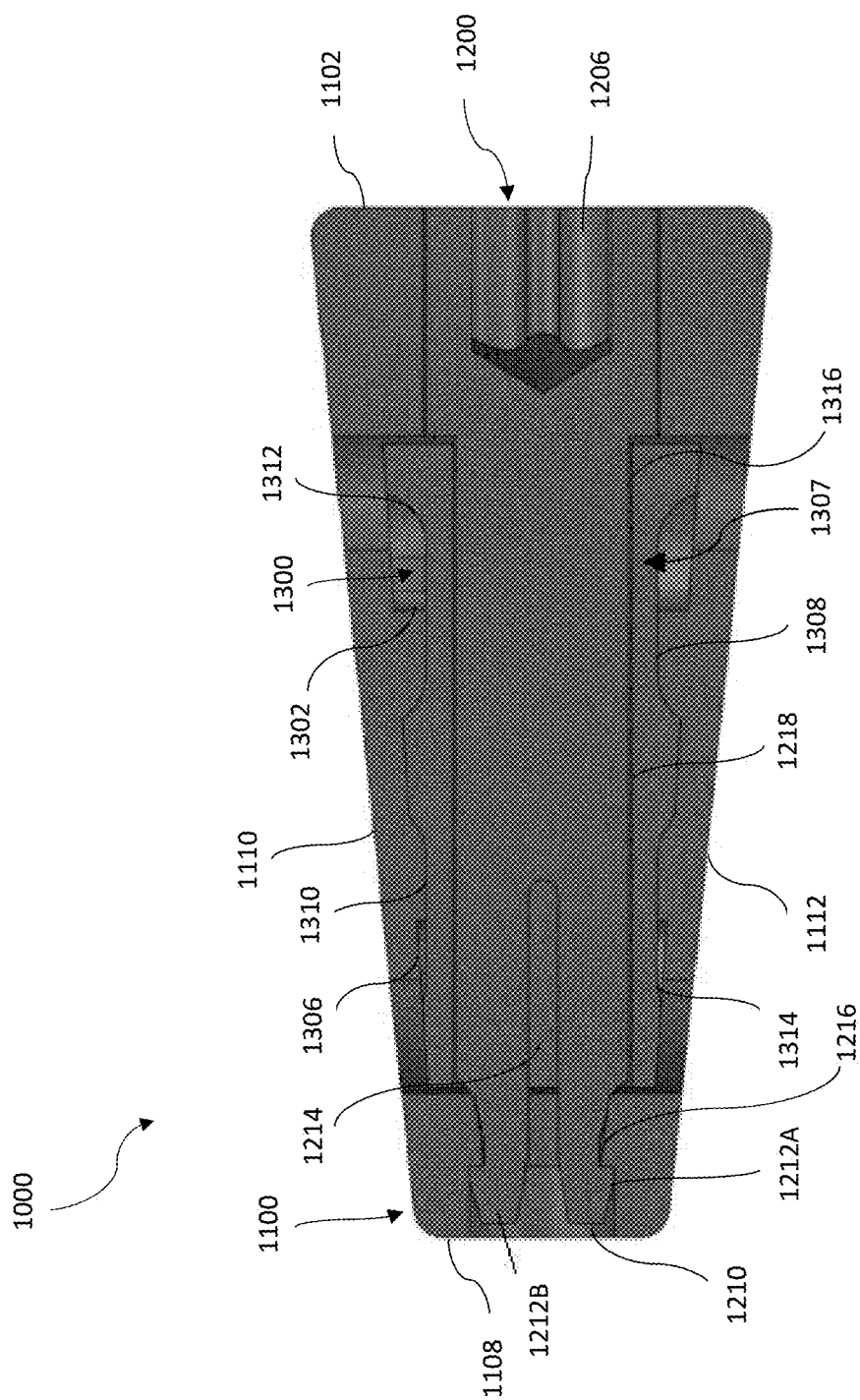
FIG. 10 is a cross-sectional side view of the device of FIG. 1, in accordance with an aspect of the present disclosure.
Figure 20:
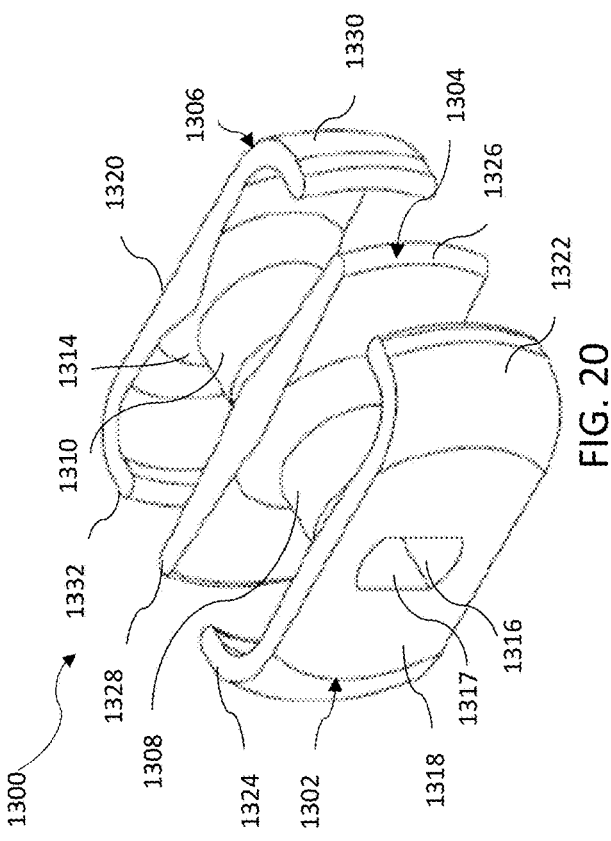
FIG. 20 is a first perspective view of the cutting member of the device of FIG. 1, in accordance with an aspect of the present disclosure.
Figure 22:
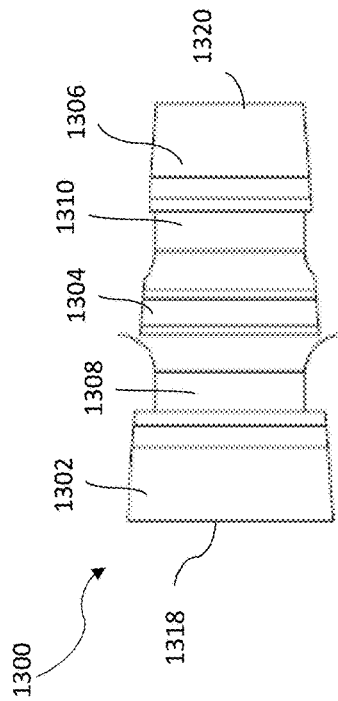
FIG. 22 is a second side view of the cutting member of the device of FIG. 1, in accordance with an aspect of the present disclosure.

As depicted FIGS. 9-10, drive shaft 1200 may be inserted into first circular aperture 1124 of apertures 1123 of wedge housing 1100, through hollow channel 1316 of central cylinder 1307, and into second circular aperture 1126 of apertures 1123 of wedge housing 1100 until a plurality of fasteners 1212, such as fastener 1211 and fastener 1213 for example, of a narrow end 1210 of drive shaft 1200 engage third side 1108 of wedge housing 1100. A passage 1214 may separate each of fasteners 1212, as shown in FIG. 9 in which passage 1214 separates fastener 1211 from fastener 1213, for example. Fasteners 1212 may, for example, be flexible such that they impinge on passage 1214 during insertion into second circular aperture 1126 of third side 1108 of wedge housing 1100. Once fully inserted into third side 1108, a groove 1216 of fasteners 1212 may partially lock drive shaft 1200 into place such that drive shaft 1200 may be inhibited from detaching from third side 1108 but still be rotatable about the axis of wedge housing 1100. Cutting member 1300 may, for example, be inserted into central cavity 1128 prior to inserting drive shaft 1200 through wedge housing 1100. Further depictions of wedge housing 1100 are shown in FIGS. 11-14. As shown in FIGS. 15-18, drive shaft 1200 may also include a shaft 1218 that includes a flat or relatively planar segment 1220 for engaging a corresponding inner wall 1317 (FIGS. 20-21) of hollow channel 1316 (FIGS. 9-10) of central cylinder 1307 (FIGS. 9-10). Additionally, shaft 1218 may also include a convexly rounded segment 1222 curved outward from shaft 1218, as depicted in FIG. 16, that is connected to relatively planar segment 1220. For instance, according to one embodiment, hollow channel 1316 may be oblong or cylindrical in shape such that relatively planar segment 1220 engages hollow channel 1316 (FIGS. 9-10) during rotation of drive shaft 1200 such that cutting member 1300 (FIG. 9) also rotates.

Figure 19:
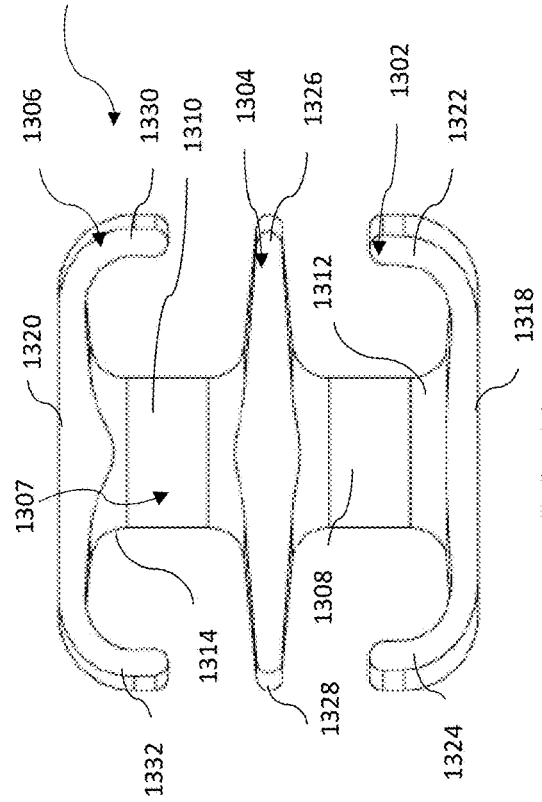
FIG. 19 is a top view of the cutting member of the device of FIG. 1, in accordance with an aspect of the present disclosure.
Figure 21:
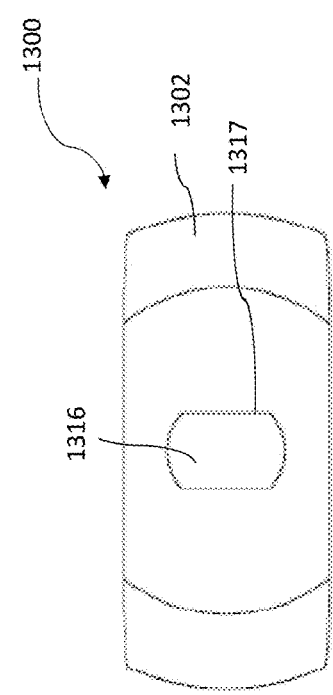
FIG. 21 is a first side view of the cutting member of the device of FIG. 1, in accordance with an aspect of the present disclosure.
Figure 26:
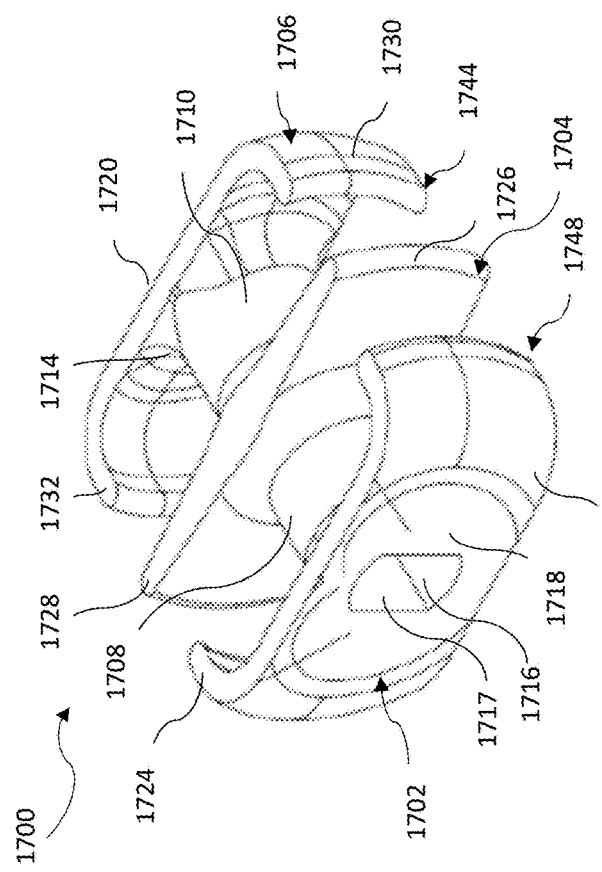
FIG. 26 is a first perspective view of the alternate cutting member for the device of FIG. 1, in accordance with an aspect of the present disclosure.
Figure 28:
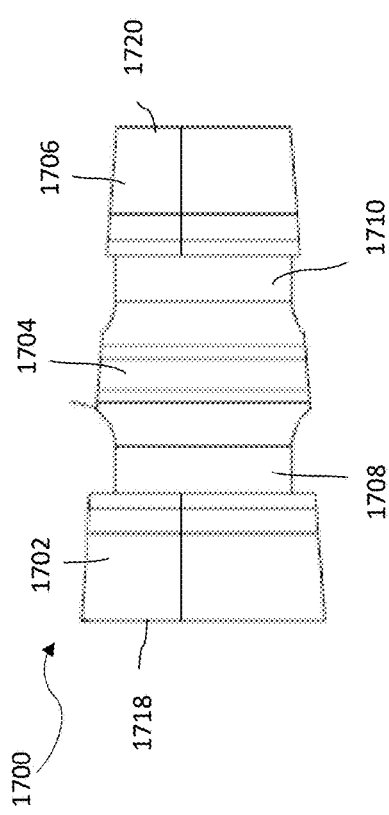
FIG. 28 is a second side view of the alternate cutting member for the device of FIG. 1, in accordance with an aspect of the present disclosure.
Figure 25:
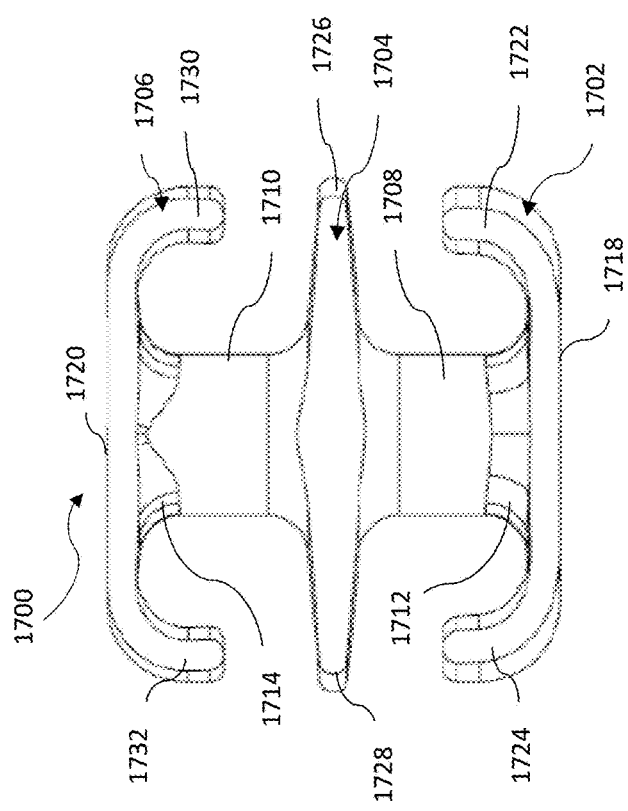
FIG. 25 is a top view of the alternate cutting member for the device of FIG. 1, in accordance with an aspect of the present disclosure.
Figure 27:
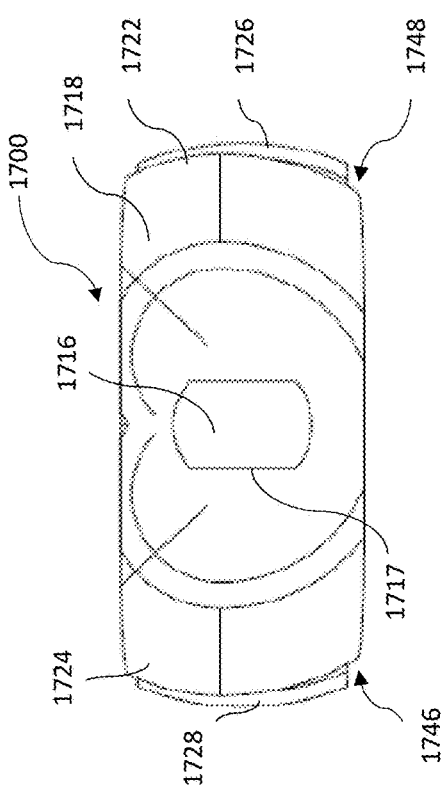
FIG. 27 is a first side view of the alternate cutting member for the device of FIG. 1, in accordance with an aspect of the present disclosure.
Figure 30:
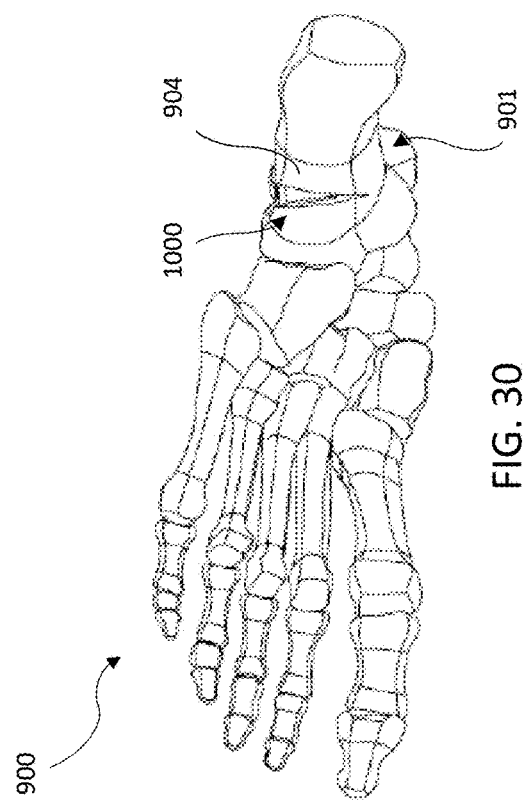
FIG. 30 is a bottom view of the patient's foot with the device of FIG. 1 implanted into the patient's calcaneus, in accordance with an aspect of the present disclosure.
Figure 32:
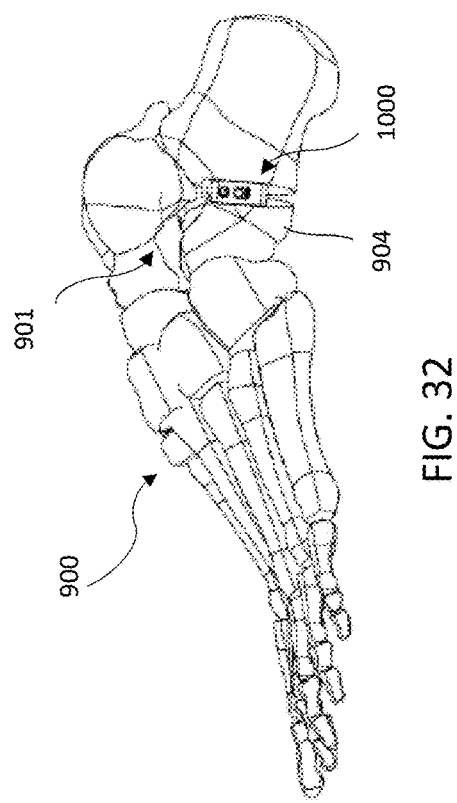
FIG. 32 is a first side view of the patient's foot with the device of FIG. 1 implanted into the patient's calcaneus, in accordance with an aspect of the present disclosure.
Figure 29:
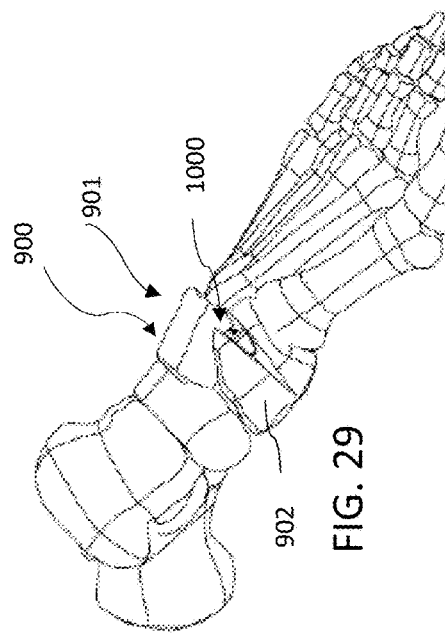
FIG. 29 is a perspective view of a patient's foot with the device of FIG. 1 implanted into the patient's medial cuneiform, in accordance with an aspect of the present disclosure.
Figure 31:
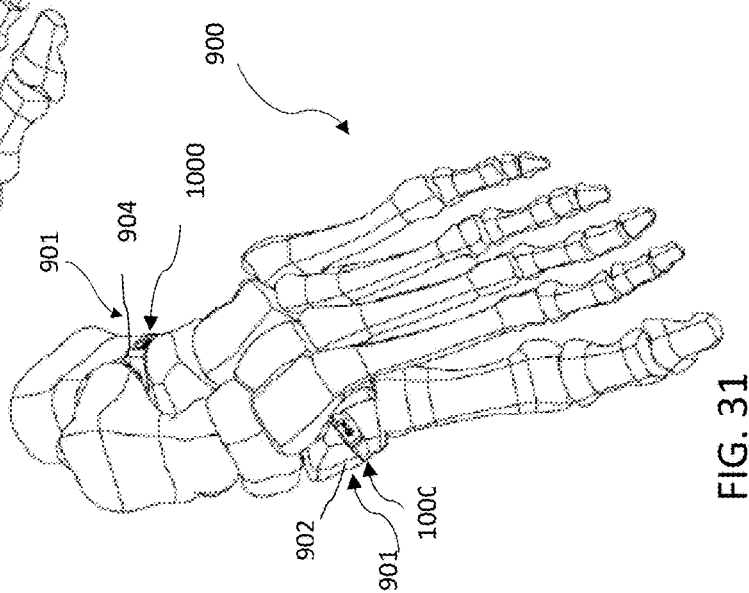
FIG. 31 is a top view of the patient's foot with the device of FIG. 1 implanted into both the patient's medial cuneiform and the patient's calcaneus, in accordance with an aspect of the present disclosure.

As shown in FIGS. 19-22, according to one embodiment, first arm 1302 of arms 1301 (FIG. 19) and third arm 1306 of arms 1301 of cutting member 1300 may hook inwardly towards second arm 1304 and second arm 1304 of arms 1301 may be relatively straight, i.e. aligned linearly in a direction about perpendicular to central cylinder 1307 as depicted in FIG. 19. First arm 1302, positioned on a front side 1318 of cutting member 1300 may include a first cutting hook 1322 and a second cutting hook 1324, second arm 1304 may include a first cutting edge 1326 and a second cutting edge 1328, and third arm 1306 positioned at a back end 1320 of cutting member 1300 may include a third cutting hook 1330 and a fourth cutting hook 1332. In alternative embodiments, second arm 1304 may also include, for example, double hooked edges such that second arm 1304 has a "T" shape at first cutting hook 1322 and another "T" shape at second cutting hook 1324.

According to one embodiment, bone wedge device 1000 may include a compression cutting member 1700, shown in FIGS. 23-28, rather than cutting member 1300 (FIGS. 19-22). Compression cutting member 1700 may be configured (e.g., sized and shaped) such that pressure is applied to the patient's bone, once inserted, to push the bone towards bone wedge device 1000. In particular, compression cutting member 1700 may include a first arm 1702 positioned on a front side 1718 of cutting member 1700 separated from a centralized second arm 1704 by a first segment 1708. Compression cutting member 1700 may also include a third arm 1706 positioned on a back side 1720 of compression cutting member 1700 and separated from second arm 1704 by a second segment 1710, where first arm 1702 and third arm 1706 are manufactured to follow a different cutting trajectory than first arm 1302 (FIGS. 19-22) and third arm 1306 (FIGS. 19-22) of cutting member 1300 (FIGS. 19-22). Additionally, a first portion 1712 (FIG. 25) may connect first arm 1702 to first segment 1708 and a second sloping portion 1714 (FIG. 25) may connect third arm 1706 to second segment 1710.

During manufacturing, a central axis 1740 of a hollow channel 1716 may be decentralized to a misaligned axis 1742 when cutting a first cutting hook 1722, a second cutting hook 1724, a third cutting hook 1730, and a fourth cutting hook 1732. Hollow channel 1716 may include an inner wall 1717 for engaging relatively planar segment 1220 (FIGS. 15-18) during rotation of compression cutting member 1700 to engage bone 901. The decentralization to misaligned axis 1742 may facilitate producing a relatively longer angular slope 1748 on first cutting hook 1722 than an opposing centralized slope 1749 of first cutting hook 1722, and a longer angular slope 1750 than an opposing centralized slope 1751 of second cutting hook 1724. Similarly, decentralization to misaligned axis 1742 may facilitate producing a relatively longer angular slope 1744 than an opposing centralized slope 1753 of third cutting hook 1730 and a relatively longer angular slope 1746 than an opposing centralized slope 1755 of fourth cutting hook 1732. Second arm 1704 may include a first cutting edge 1726 and a second cutting edge 1728 that are not offset relative each other and may maintain central axis 1740 during manufacturing. Having longer angular slopes 1744, 1746, 1748, 1750 such that cutting angles of first cutting hook 1722 and second cutting hook 1724 are off-center may, according to one embodiment, inhibit separation of the bone when drive shaft 1200 begins to be rotated. In particular, separation is inhibited when longer angular slopes 1744, 1746, 1748, 1750 cut into the bone at different paths than centralized slopes 1749, 1751, where the different paths may facilitate maintaining position of bone wedge device 1000 once inserted.

Figure 33:
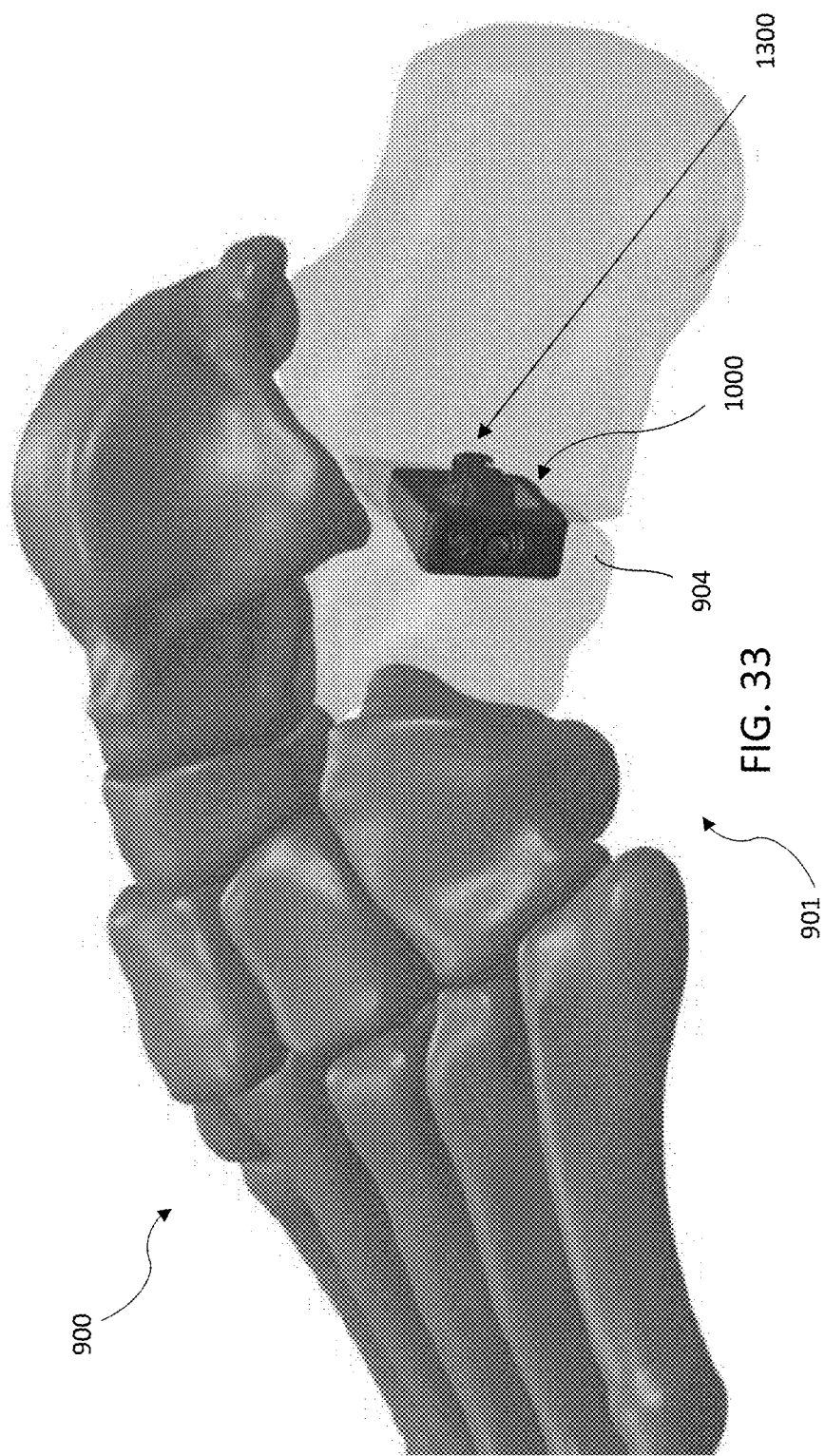
FIG. 33 is a first side view of the patient's foot with the cutting member of the device of FIG. 1 engaged with the patient's calcaneus, in accordance with an aspect of the present disclosure.

FIGS. 29-33 depict bone wedge device 1000 implanted into bone 901 of foot 900. As indicated above, bone 901 may include, for example, medial cuneiform 902 of the patient and/or calcaneus 904 of the patient. FIG. 33 further depicts cutting member 1300 engaged with calcaneus 904 of the patient.

Figure 34:
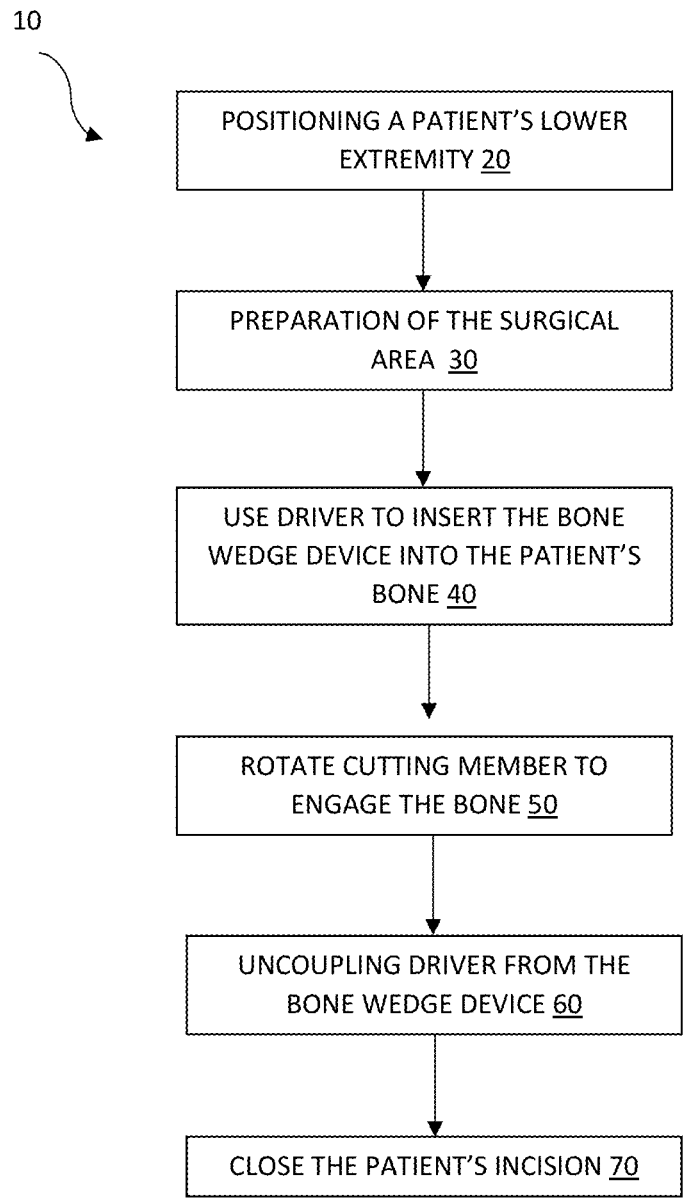
FIG. 34 depicts a surgical method, in accordance with aspects of the present disclosure.

FIG. 34 depicts a surgical method 10 according to one embodiment. The surgical method may include a step 20 of positioning of a patient's lower extremity and a step 30 of preparing a surgical area. Step 30 of preparing the surgical area may include, for example, surgically exposing a portion of the patient's foot to expose the patient's medial cuneiform and/or the patient's calcaneus. The surgical method may include a step 40 of using a driver (not shown) to insert bone wedge device 1000 into the patient's bone. Further, the cutting member may be rotated, a step 50, to engage the bone. The driver (not shown) may be uncoupled, a step 60, from the bone wedge device, and the patient's incision may be closed, a step 70.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An osteotomy implant device, said osteotomy implant device comprising:
   a wedge shaped housing, said wedge shaped housing including a top side, a bottom side, a front side, a back side, a right side and a left side, said wedge shaped housing defining an inner cavity by the front side, the back side, the right side and the left side that is open through the top side and the bottom side, said wedge shaped housing including a central plane, at least one of the top side and the bottom side extending at an acute angle relative to the central plane;
   a drive shaft, said drive shaft rotatable about an axis, said drive shaft rotatably coupled to said wedge shaped housing, said drive shaft including an elongated body extending from a head to a distal end, the head of said drive shaft rotatable within a through aperture formed in the front side of said wedge shaped housing, the distal end of said drive shaft rotatably coupled in an aperture defined in a cavity wall of the back side of said wedge shaped housing; and
   a cutting member, said cutting member coupled to and rotatable with said drive shaft between a first position and a second position, said cutting member including a first set of fins extending radially outward from the axis in a first direction and a second set of fins extending radially outward from the axis in a second direction, wherein the first direction is opposite the second direction, each fin of the first set of fins is spaced from an adjacent fin along the axis, each fin of the second set of fins is spaced from an adjacent fin along the axis, the first set of fins and the second set of fins entirely disposed within the cavity between the top side and the bottom side in the first position, wherein at least a portion of the first set of fins extends beyond the top side and at least a portion of the second set of fins extends beyond the bottom side of said wedge shaped housing in the second position, wherein said drive shaft extends between the front side and the back side of said wedge shaped housing through a hollow channel defined by said cutting member along the axis.

2. The osteotomy implant device of claim 1, wherein the fins of the first set of fins and the second set of fins radially extend substantially along the central plane in the first position.

3. The osteotomy implant device of claim 2, wherein each fin of the first set of fins and the second set of fins includes a distal end, the distal ends of at least one of the fins in each of the first set of fins and the second set of fins includes a hook portion.

4. The osteotomy implant device of claim 1, wherein, in the second position, the fins of the first set of fins and the second set of fins radially extend substantially perpendicular to the central plane of said wedge shaped housing.

5. An osteotomy implant device, said osteotomy implant device comprising:
   a wedge shaped housing, said wedge shaped housing including a top side, a bottom side, a front side, a back side, a right side and a left side, said wedge shaped housing defining an inner cavity by the front side, the back side the right side and the left side that is open through the top side and the bottom side, said wedge shaped housing including a central plane, at least one of the top side and the bottom side extending at an acute angle relative to the central plane;
   a drive shaft, said drive shaft rotatable about an axis, said drive shaft rotatably coupled to said wedge shaped housing, said drive shaft including an elongated body extending from a head to a distal end, the head of said drive shaft rotatable within a through aperture formed in the front side of said wedge shaped housing, the distal end of said drive shaft rotatably coupled in an aperture defined in a cavity wall of the back side of said wedge shaped housing; and
   a cutting member, said cutting member coupled to and rotatable with said drive shaft between a first position and a second position, said cutting member including a first set of fins extending radially outward from the axis in a first direction and a second set of fins extending radially outward from the axis in a second direction, wherein the first direction is opposite the second direction, each fin of the first set of fins is spaced from an adjacent fin along the axis, each fin of the second set of fins is spaced from an adjacent fin along the axis, the first set of fins and the second set of fins entirely disposed within the cavity between the top side and the bottom side in the first position, wherein at least a portion of the first set of fins extends beyond the top side and at least a portion of the second set of fins extends beyond the bottom side of said wedge shaped housing in the second position, wherein the fins of the first set of fins and the second set of fins radially extend substantially along the central plane in the first position, wherein the through aperture formed in the front side of said wedge shaped housing includes a first channel and a second channel defined by a flexible appendage positioned within the through aperture, the flexible appendage configured to be displaced into the first channel or the second channel by a protrusion formed on the head of said drive shaft as a result of rotation of said drive shaft.

6. An osteotomy implant device, said osteotomy implant device comprising:
   a housing, said housing defining a cavity and having a central plane extending therethrough, said housing including a first side and a second side, the second side disposed on an opposing side of the central plane from the first side;
   a drive shaft, said drive shaft rotatably coupled to said housing; and
   a cutting member, said cutting member coupled to and rotatable with said drive shaft, said cutting member rotatable between a first position and a second position, said cutting member including a plurality of fins extending radially outward, the plurality of fins entirely disposed within the cavity between the first side and the second side in the first position, wherein at least a portion of the plurality of fins extends beyond at least the first side or the second side of said housing in the second position wherein said cutting member includes a longitudinal axis, wherein said cutting member includes at least three fins extending radially outward from, and spaced apart from each other along, the longitudinal axis in a first direction and at least three fins extending radially outward from, and spaced apart from each other along, the longitudinal axis in a second direction, wherein the first direction is opposite the second direction, wherein each of the plurality of fins includes a distal free end, the distal free end of at least one of the plurality of fins including a hook portion.

7. A method for wedge osteotomy of a foot, said method comprising the steps of:
   exposing a portion of the foot;
   providing an osteotomy implant device, said osteotomy implant device comprising:
   a housing, said housing defining a cavity and having a central plane extending therethrough, said housing including a first side and a second side, the second side disposed on an opposing side of the central plane from the first side;
   a drive shaft, said drive shaft rotatably coupled to said housing, the drive shaft including a head defining a socket; and
   a cutting member, said cutting member coupled to and rotatable with said drive shaft, said cutting member rotatable between a first position and a second position, said cutting member including a plurality of fins extending radially outward, the plurality of fins entirely disposed within the cavity between the first side and the second side in the first position, wherein at least a portion of the plurality of fins extends beyond at least the first side or the second side of said housing in the second position;
   inserting the osteotomy implant device in the first position into bone in the exposed portion of the foot;
   inserting a driver into the socket of the head of said drive shaft; and
   rotating the driver which rotates said drive shaft and cutting member towards the second position so that the plurality of fins engage the bone.

8. The method of claim 7, wherein at least one of the plurality of fins includes a hook portion at a distal end of the fin.

* * * * *